United States Patent
Chodorge et al.

[11] Patent Number: 6,159,433
[45] Date of Patent: Dec. 12, 2000

[54] PLANT FOR THE CONVERSION OF OLEFINIC $C_4$ AND $C_5$ CUTS TO AN ETHER AND TO PROPYLENE

[75] Inventors: Jean-Alain Chodorge, Antony; Dominique Commereuc, Meudon; Jean Cosyns, Maule; Didier Duee, Eragny sur Oise; Bernard Torck, Boulogne sur Seine, all of France

[73] Assignee: Institut Francais du Petrole, Rueil-Malmaison, Cedex, France

[21] Appl. No.: 09/184,079

[22] Filed: Nov. 2, 1998

Related U.S. Application Data

[62] Division of application No. 08/644,196, May 10, 1996, Pat. No. 5,898,091.

[30] Foreign Application Priority Data

May 11, 1995 [FR] France .................................. 95 05561

[51] Int. Cl.[7] .......................................................... B01J 8/04
[52] U.S. Cl. ........................................ 422/189; 422/188
[58] Field of Search ................................... 422/188, 189, 422/211; 585/251, 253, 264, 615, 651, 324, 315

[56] References Cited

U.S. PATENT DOCUMENTS

| | | | |
|---|---|---|---|
| 3,660,506 | 5/1972 | Banks | 260/666 |
| 4,481,377 | 11/1984 | Kukes et al. | 585/646 |
| 4,513,153 | 4/1985 | Sandrin | 568/647 |
| 4,665,245 | 5/1987 | Quann | 585/316 |
| 4,695,662 | 9/1987 | Vora | 505/655 |
| 4,754,078 | 6/1988 | Vora | 585/331 |
| 5,026,935 | 6/1991 | Leyshon et al. | 585/315 |
| 5,026,936 | 6/1991 | Leyshon et al. | 585/315 |
| 5,120,894 | 6/1992 | McCauley | 585/664 |
| 5,124,465 | 6/1992 | Allen et al. | 585/664 |
| 5,254,790 | 10/1993 | Thomas et al. | 585/664 |
| 5,300,718 | 4/1994 | McCaulley | 585/324 |
| 5,519,101 | 5/1996 | Nubel | 585/646 |
| 5,523,502 | 6/1996 | Rubin | 585/324 |
| 5,675,051 | 10/1997 | Chauvin et al. | 585/646 |

FOREIGN PATENT DOCUMENTS

| | | |
|---|---|---|
| 0 605 822 | 7/1994 | European Pat. Off. |
| 94/08922 | 4/1994 | WIPO |

*Primary Examiner*—Marian C. Knode
*Assistant Examiner*—Susan Ohorodnik
*Attorney, Agent, or Firm*—Millen, White, Zelano & Branigan

[57] ABSTRACT

The present invention concerns a plant for the conversion of an olefinic $C_4$ or $C_5$ cut to an alkyl-tertiobutylether or alkyl-tertioamylether and to propylene, by metathesis. The plant comprises four successive stages: (1) selective hydrogenation of the diolefins with simultaneous isomerisation of the alpha olefins to internal olefins; (2) etherification of the isoolefins; (3) elimination of oxygen-containing impurities; (4) metathesis of internal olefins with ethylene. Application to $C_4$ and $C_5$ steam cracking units.

14 Claims, 3 Drawing Sheets

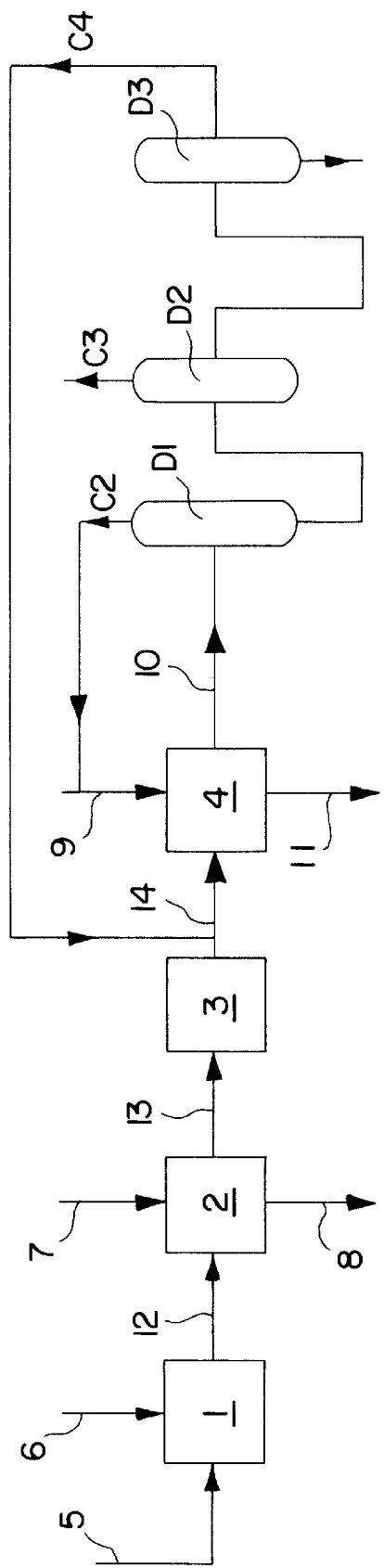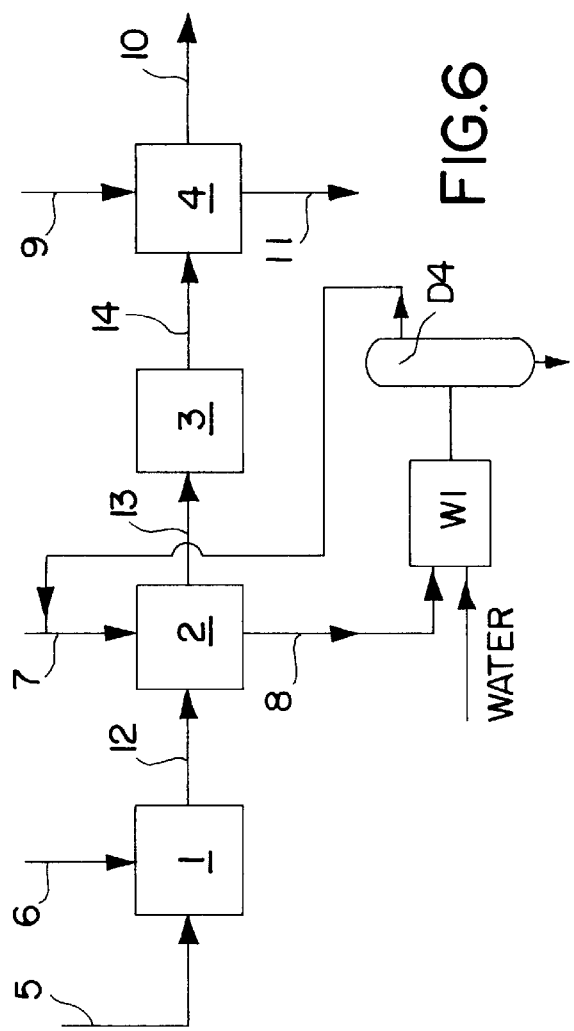

PLANT FOR THE CONVERSION OF OLEFINIC $C_4$ AND $C_5$ CUTS TO AN ETHER AND TO PROPYLENE

This application is a divisional application of application U.S. Ser. No. 08/644,195 filed May 10, 1996, now U.S. Pat. No. 5,898,091 issued Apr. 27, 1999.

BACKGROUND OF THE INVENTION

The aim of the present invention is to provide a plant for the conversion of at least one cut selected from the group formed by olefinic $C_4$ cuts and olefinic $C_5$ cuts to an ether (an alkyl-tertiobutylether or an alkyl-tertioamylether) and to propylene. When the cut originates from a steam cracking operation, a further aim of the present invention is to optimise the relative ethylene-propylene selectivity of the steam cracking procedure using this plant.

Steam cracking of feeds constituted by light paraffin cuts supplies ethylene and propylene for the petrochemical industry. It also provides a number of other heavier products, in particular a $C_4$ hydrocarbon cut which contains mainly 1,3-butadiene, isobutene, n-butenes and butanes, accompanied by traces of acetylenic hydrocarbons, and a $C_5$ hydrocarbon cut which contains mainly $C_5$ diolefins, methylbutenes, n-pentenes and pentanes, accompanied by traces of acetylenic hydrocarbons.

As well as the principal products of petrol and gas oil fractions, catalytic cracking of heavy hydrocarbon feeds, in particular fluid catalytic cracking (FCC), produces lighter products, among them a $C_4$ hydrocarbon cut which contains mainly isobutane, isobutene, n-butenes and butanes, accompanied by small quantities of 1,3-butadiene and acetlyenic hydrocarbons, and a $C_5$ hydrocarbon cut which contains mainly pentanes, methylbutenes and n-pentenes, accompanied by small quantities of $C_5$ diolefins and acetlyenic hydrocarbons.

Until recently, only 1,3-butadiene and isobutene were of use in the polymer industry, in particular in the tire industry for the former. An increase in tire lifetime and a relative stagnation of demand has led to a surplus of butadiene which is not used to any great extent. In contrast, isobutene has gained in importance as it can be used to synthesize ethers which are used as additives for motor fuels.

The present invention provides a plant for the treatment of a $C_4$ hydrocarbon cut containing mainly isobutene, n-butenes, butanes and varying amounts of 1,3-butadiene, which includes the transformation of isobutene to ethers (for example MTBE), and which can transform 1,3-butadiene and n-butenes to propylene for polymerisation, for example. It also provides a plant for the treatment of a $C_5$ cut to transform it primarily into ethers (for example TAME) and propylene. It further provides a plant for the combined treatment of a $C_4$ cut and a $C_5$ cut.

The relative proportions of ethylene and propylene produced in a steam cracking operation can be modulated to a certain extent by changing the nature of the feed and modifying the cracking conditions (severity). However, one operating mode intended to produce a higher proportion of propylene inevitably produces larger quantities of $C_4$ Cut, $C_5$ cut and heavier petrol fractions of poor quality.

A further aim of the present invention is to optimise the relative ethylene-propylene selectivity of the steam cracking procedure by treating the $C_4$ or $C_5$ steam cracking hydrocarbon cuts to produce, inter alia, propylene, thus enabling the relative proportions of ethylene and propylene to be adjusted without being obliged to change the cracking severity.

More precisely, the object of the invention is to provide a plant for the conversion of at least one olefinic cut, selected from the group formed by a $C_4$ cut and a $C_5$ cut, to an ether and to propylene, the cuts containing mainly diolefins, alpha olefins, isoolefins and acetylenic impurities the already patented process comprises the following steps which are carried out successively:

1) selective hydrogenation of the diolefins and acetylenic impurities with simultaneous isomerisation of the alpha olefins to internal olefins by passing said cut in the liquid phase over a catalyst comprising at least one metal selected from the group formed by nickel, palladium and platinum, deposited on a support, at a temperature of 20–200° C., a pressure of 1–5 MPa, and a space velocity of 0.5–10 $h^{-1}$, with a $H_2$/diolefin (molar) ratio of 0.5 to 5, preferably 1 to 3, to obtain an effluent containing mainly internal olefins and isoolefins, and containing practically no diolefins or acetylenic compounds;

2) etherification of the isoolefins by reacting the effluent from the preceding step with an alcohol, in the presence of an acid catalyst, at a temperature of 30–130° C., at a pressure such that the reaction is carried out in the liquid phase, the ether and alcohol being separated simultaneously with or after etherification to obtain an effluent containing mainly internal olefins accompanied by oxygen-containing impurities;

3) separation of the oxygen-containing impurities from the effluent from step 2);

4) metathesis of the effluent from the preceding step with ethylene, in the presence of a catalyst comprising at least one rhenium oxide deposited on a support, at a temperature in the range 0° C. to 100° C., and at a pressure which is at least equal to the vapour tension of the reaction mixture at the reaction temperature, to obtain an effluent containing propylene, the metathesis being followed by separation of the propylene.

The process aspect of the invention (illustrated in FIG. 1) will be described in more detail using a $C_4$ hydrocarbon cut containing mainly isobutene, n-butenes, butanes, and varying amounts of 1,3-butadiene, supplied via a line 5. The $C_4$ cut undergoes a succession of treatments which are consolidated in the following steps, to produce an alkyl-tertiobutylether and propylene:

selective hydroisomerisation of 1,3-butadiene with isomerisation of 1-butene to 2-butene and hydrogenation of acetylenic hydrocarbons;

etherification with an alcohol to produce an alkyl-tertiobutylether;

separation of oxygen-containing compounds;

metathesis of the 2-butene-rich effluent in the presence of ethylene (ethenolysis) to produce propylene.

The succession of treatments of the process of the invention has a number of advantages. The most reactive compounds in the cut, namely the diolefins (for example 1,3-butadiene) which are in varying amounts, and the traces of acetylenic hydrocarbons, are transformed in the first step and thus do not cause side reactions in the following steps. Further, selective hydroisomerisation of diolefins (for example 1,3-butadiene) in the steam cracking cuts can considerably increase the concentration of the corresponding internal olefin (2-butene in this case) in the cut, further enhancing the metathesis step and producing a high yield of propylene.

The principal aim of the first step is to transform 1,3-butadiene and n-butenes into 2-butene. 2-butene is the source of the propylene which is produced in the last metathesis step in the presence of ethylene. 1-butene does not produce a new product with the ethylene, and reacts with the 2-butene to produce propylene, but also to produce undesirable pentenes. Maximising the yield of 2-butene is thus desirable, i.e., to get as close as possible to the proportions dictated by thermodynamics. The second aim of this step is to eliminate the traces of acetylenic hydrocarbons which are always present in these cuts and which poison or pollute the subsequent steps.

In the first step (zone 1), the following reactions are carried out simultaneously, in the presence of hydrogen supplied via line 6:

selective hydroisomerisation of 1,3-butadiene to a mixture of n-butenes in thermodynamic equilibrium;

isomerisation of 1-butene to 2-butene, also in thermodynamic equilibrium;

hydrogenation of traces of acetylenic hydrocarbons.

These reactions can be carried out using various specific catalysts comprising one or more metals, for example from group 10 of the periodic classification (Ni, Pd, Pt), deposited on a support. Preferably, a catalyst is used which comprises at least one palladium compound fixed on a refractory mineral support, for example alumina. The amount of palladium on the support can be in the range 0.01% to 5% by weight, preferably in the range 0.05% to 1% by weight. A variety of known pretreatments may be applied to these catalysts to improve selectivity for the hydrogenation of 1,3-butadiene to butenes at the expense of complete hydrogenation to butane which must be avoided. The catalyst preferably contains 0.05% to 10% by weight of sulphur. Advantageously, the catalyst is constituted by palladium deposited on alumina and containing sulphur.

The catalyst can be sulphurized in situ (in the reaction zone) or preferably ex situ. In the latter case, the process described in French patent FR-93/09524 is preferably used, where the catalyst is treated, before being charged into the hydrogenation reactor, with at least one sulphur-containing compound diluted in a solvent, and the catalyst obtained containing 0.05% to 10% of sulphur (by weight) is charged into the reactor and activated in a neutral or reducing atmosphere at a temperature in the range 20° C. to 300° C., at a pressure in the range 0.1 to 5 MPa and at a GHSV in the range 50 to 600 h$^{-1}$, where the feed is brought into contact with the activated catalyst.

The mode of use of the catalyst, which is preferably of palladium, is not critical, but it is generally preferred to use at least one downflow reactor with a fixed bed of catalyst. When the proportion of 1,3-butadiene in the cut is high, as is the case, for example, for a steam cracking cut when the 1,3-butadiene is not to be extracted for specific purposes, it may be of advantage to effect the transformation in two reactors in series to better control the hydrogenation selectivity. The second reactor may be an upflow reactor and may act as a finisher.

The quantity of hydrogen required for the reactions carried out in this step is adjusted as a function of the composition of the cut so that, advantageously, there is only a slight excess of hydrogen with respect to the theoretical stoichiometry.

The operating conditions are selected so that the reactants and products are liquid. It may, however, be of advantage to select an operating mode such that the products are partially vaporised at the reactor outlet, to facilitate thermal control of the reaction. The temperature can be between 20° C. and 200° C., preferably between 50° C. and 150° C., or more preferably between 60° C. and 150° C. The pressure can be adjusted to between 0.1 and 5 MPa, preferably between 0.5 and 4 MPa, advantageously between 0.5 and 3 MPa, so that the reactants are at least partially in the liquid phase. The space velocity can be in the range 0.5 to 10 h$^{-1}$, preferably in the range 1 to 6 h$^{-1}$, with a H$_2$S/diolefin (molar) ratio of 0.5 to 5, preferably 1 to 3.

Advantageously, the hydroisomerisation reactor or reactors is/are followed by a stabilizing column which eliminates traces of excess hydrogen and any methane.

The aim of the second step (zone 2) is to transform the isobutene present in the C$_4$ cut from the preceding step into an alkyl-tertiobutylether by etherification with an alcohol having a hydrocarbon chain which can contain 1 to 10 carbon atoms, supplied via line 7. The alcohol is preferably methanol or ethanol. The ethers produced are respectively methyl-tertiobutylether (MTBE) and ethyl-tertiobutylether (ETBE), which leave via line 8.

Transformation is carried out using an acid catalyst, for example a catalyst based on an ion exchange resin in its H-form, such as a sulphonic acid resin—SO$_3$H. This catalyst can be used, for example, in a conventional fixed bed or in a mobile bed. An expanded catalyst bed is preferably used, maintained by an upflow of reaction medium through the reactor and an external heat exchanger. This type of operation can readily control the catalyst and eliminate the heat produced during, the reaction, by preventing the formation of hot spots.

A finishing reactor is advantageously located after the expanded bed reactor to maximise removal of isobutene from the residual cut and to increase the yield of ether, but the majority of the reaction occurs in the expanded bed reactor. A maximum amount of isobutene can also be removed by using reactive distillation in the finisher (a distillation column containing a catalyst) which can increase conversion by separating the products in the reactor.

The operating conditions are selected so that the reactants and products are in the liquid phase. In general, the temperature is fixed so that the reaction occurs at a sufficient rate, for example 30° C. to 130° C., preferably 40° C. to 100° C., and the pressure is adjusted as a consequence so that the reactants are in the liquid phase.

The reaction section is followed by a distillation section where the ether is separated at the bottom of the column from a distillate comprising the residual C$_4$ cut and excess alcohol, also traces of other volatile oxygen-containing compounds. Referring to FIG. 6, the alcohol is separated by washing with water (W1) and the water-alcohol mixture is distilled (D4) to recycle the alcohol.

The C$_4$ cut from the etherification step contains a small amount of a certain number of oxygen-containing and sulphur-containing compounds which must be separated in a third step (zone 3) of the process since these are poisons which reduce the efficiency of the metathesis catalysts.

A variety of methods can be used to carry out the separation. Preferably, the C$_4$ cut from the etherification step is passed over a capture mass which has a higher affinity for oxygen-containing compounds than for olefinic or saturated hydrocarbons, and which can be constituted by refractory oxides and/or aluminosilicates which have an acidic nature, such as alumina, silica, silica-aluminas, or zeolites. When the etherification step uses methanol, it may be of advantage, in order to reduce the volume of the capture mass, to precede this step by a distillation column which separates the dimethylether which is a by-product of etherification and which dries the C$_4$ cut at the same time.

The capture mass is used in a fixed bed, for example, and under temperature and pressure conditions such that the feed and the effluent are in the liquid phase. The temperature is in the range 0° C. to 100° C., preferably in the range 10° C. to 50° C. The pressure is in the range 0.3 to 5 MPa, preferably in the range 0.4 to 1 MPa. The space velocity is adjusted to obtain maximum capture of the oxygen-containing and sulphur-containing compounds.

When the capture mass is saturated with oxygen-containing and/or sulphur-containing compound, it must be regenerated, for example by entraining the adsorbed compounds in a hot gas stream. The gas can, for example, be nitrogen, methane or any gas which is inert towards the capture mass. The regeneration temperature can be in the range 200° C. to 500° C., preferably in the range 250° C. to 450° C. In order not to interrupt the continuous process, two capture masses can be used which operate alternately.

The majority of the cut obtained after the above succession of steps is constituted by butanes and 2-butene. In the final step (zone 4) of the process, the 2-butene is reacted with ethylene supplied via line 9 to produce propylene by metathesis (leaving via line 10). A line 11 evacuates the separated by-products.

The metathesis reaction of ethylene with 2-butene can be catalysed by various metal oxides deposited on supports. Preferably, a catalyst is used which comprises at least one rhenium oxide deposited on a support composed of a refractory oxide containing at least alumina, which has an acidic character, such as alumina itself, silica-aluminas or zeolites.

Preferred examples are catalysts comprising rhenium heptoxide deposited on a gamma alumina analogous to that used in reforming catalysts, as described in U.S. Pat. No. 4,795, 734. The rhenium content (expressed as rhenium metal) can be in the range 0.01% to 20%, preferably in the range 1% to 15% by weight. The catalysts are, for example, subjected to final thermal activation at a temperature in the range 400° C. to 1000° C. for a period of 10 minutes to 5 hours in a non-reducing atmosphere.

Catalysts comprising rhenium heptoxide deposited on an alumina can also be modified by addition of an oxide of another metal. These modified catalysts contain, for example, rhenium as an oxide, 0.01% to 20% by weight expressed as rhenium metal, deposited on a support containing at least 75% by weight of alumina and 0.01% to 30% by weight of at least one oxide of a metal selected from the group formed by niobium and tantalum, as described in French patent FR-A-2 709 125.

The metathesis reaction is preferably carried out in the liquid phase, in the absence of oxygen, oxygen-containing compounds and moisture, and at a temperature in the range 0° C. to 200° C., preferably in the range 20° C. to 150° C., at a pressure at least equal to that of the vapour tension of the reaction mixture at the reaction temperature.

The catalyst can be used in a fixed bed. However, since it must be regenerated frequently, it would then be necessary to use at least two reactors in parallel, one in operational mode while the other is in regenerational mode. Preferably, a catalytic mobile bed system as described in French patent FR-A-2 608 595 is used. The catalyst is extracted at regular intervals from the bottom of the reactor and transferred continuously to a regeneration system, from which it is sent to the top of the reactor.

Because of thermodynamic limitations, unconverted ethylene is fractionated in a first distillation column (D1) and recycled to the metathesis reactor. A second distillation column (D2) separates the propylene and a third column (D3) separates the unconverted $C_4$ hydrocarbons which can be recycled to the metathesis reactor, also a small quantity of a heavier fraction.

DETAILED DESCRIPTION OF THE DRAWINGS

FIG. 5 depicts three distillation columns (D1, D2, and D3) for fractionating the product leaving the first metathesis zone in line 10.

FIG. 6 depicts washing (W1) and distilling (D4) alcohol from line 8.

Figure 1:
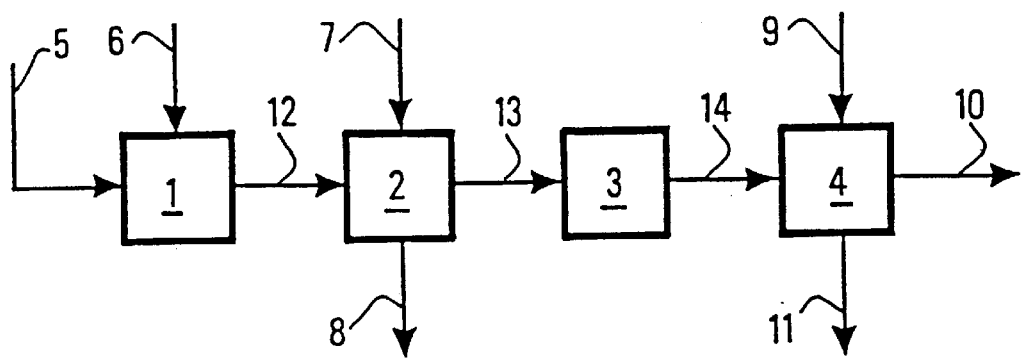
FIGS. 1–4 are all block flowsheets illustrating various embodiments of the invention.

The description of the process shown in FIG. 1 which has just been described for the $C_4$ cut, is completely applicable to the $C_5$ cut. In the first step, pentadienes are selectively hydrogenated to monoolefins and alpha olefins are isomerised to internal olefins, i.e., to 2-pentene and 2-methyl-2-butene. Etherification produces an alkyl-tertioamylether, in particular TAME (tertioamylmethylether) if the reaction is carried out with methanol. Metathesis with ethylene produces a mixture of propylene, isobutene and 1-butene. The propylene is separated from the other products, for example by distillation.

The process can also be carried out on the $C_4$ cut and the $C_5$ cut simultaneously, as described above. It may thus be of advantage to mix with the $C_4$ cut, the fraction containing mainly 1-butene and isobutene obtained by distillation of the effluent from the metathesis of the $C_5$ cut, as shown in FIG. 2.

Figure 2:
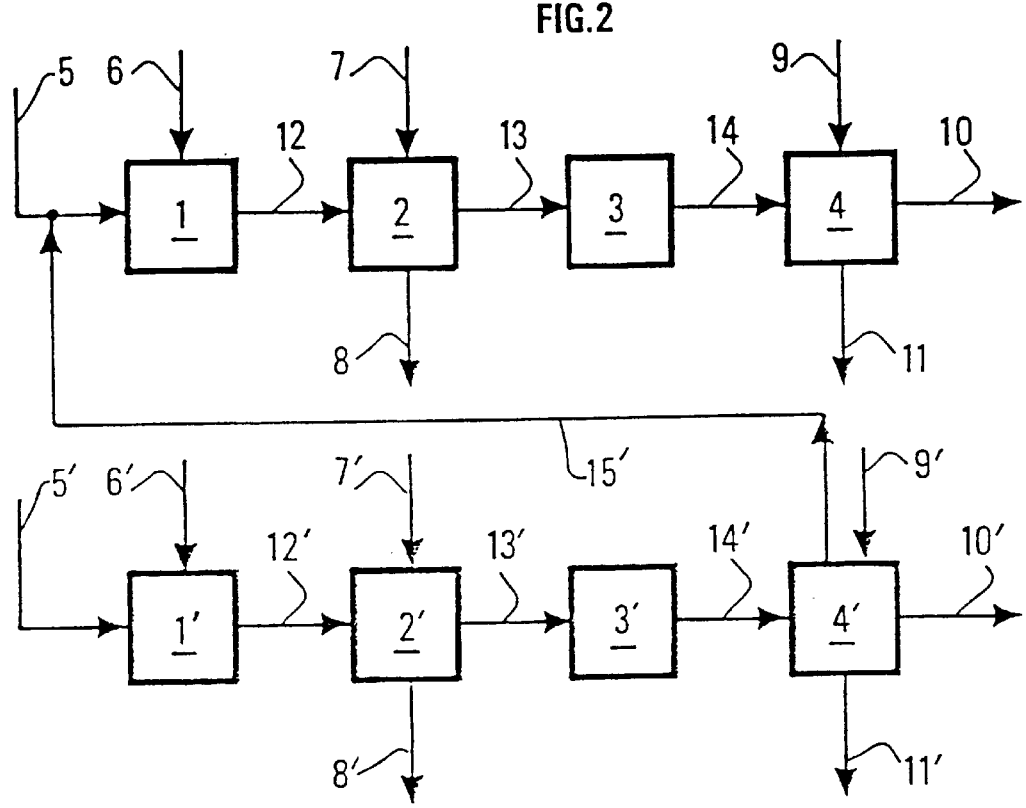

FIG. 2 illustrates a process of the invention in which the $C_4$ cut and the $C_5$ cut are treated simultaneously and separately.

The $C_5$ cut supplied via line 5' undergoes selective hydrogenation step 1' (zone 1') with hydrogen supplied via line 6', then passes to an etherification step 2' (zone 2') with alcohol supplied via line 7' and producing an alkyl-tertioamylether which leaves via line 8', followed by a step 3' for the separation of oxygen-containing impurities (zone 3') and then to a metathesis step 4' (zone 4') with ethylene supplied via line 9' to produce propylene which leave via line 10'. The separated by-products are discharged via line 11' and a mixture of 1-butene and isobutene are evacuated via line 15'.

The $C_4$ cut undergoes steps 1, 2, 3 and 4 described above with reference to FIG. 1. Steps 1, 2, 3, 4 and 1', 2', 3' and 4' are carried out using the process parameters described above.

The $C_4$ cut to be treated and the 1-butene and isobutene mixture from step 4' enter selective hydrogenation step 1 (zone 1). The mixture is introduced into zone 1 via line 15', for example, along with the $C_4$ cut.

Figure 3:
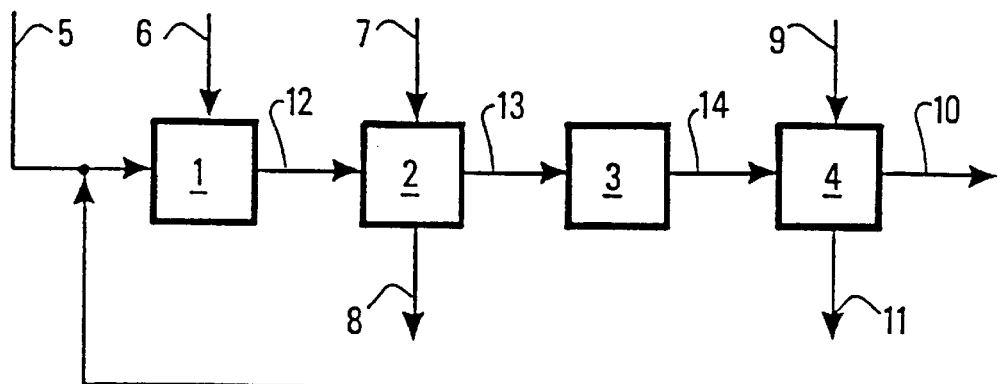

In this case, it may be of interest to omit the etherifcation step and step for separating the oxygen-containing compounds from the $C_5$ treatment line, to increase the quantity of isobutene produced which is returned to the $C_4$ treatment line. This is shown in FIG. 3. The reference numerals of FIG. 2 are used here. The $C_4$ cut and the $C_5$ cut are thus treated simultaneously and separately. The $C_5$ cut only undergoes a selective hydrogenation step 1' (zone 1') followed by a metathesis step 4' (zone 4'). These two steps are carried out under the conditions described above. Propylene is thus obtained, and a mixture of isobutene and 1-butene which is introduced with the $C_4$ cut into step 1. Thus there is no alkyl-tertioamylether production.

Figure 4:
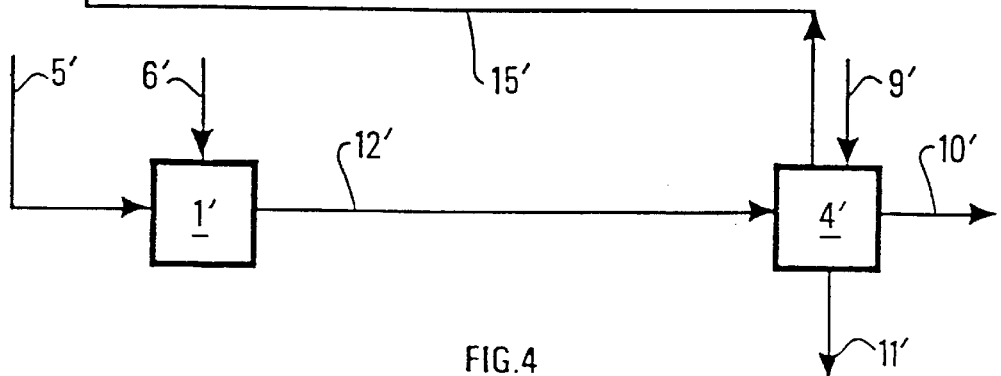

In still more simplified fashion, it may be of advantage to mix the effluents from steps 3 and 3' on the $C_4$ and $C_5$ lines (or the effluent from step 3 in the $C_4$ line with the effluent from step 1' in the C₅ line if this line omits the etherification step) so that only one metathesis operation 4 is required which is common to the two lines, as shown in FIG. 4. The dotted lines indicate the ensemble of steps 2' and 3' which do not have to be used, as shown in FIG. 3.

When the process is applied to a C₄ or C₅ steam cracking cut, it may be of advantage to integrate the metathesis unit with the cracker to benefit the fractionation string of the latter.

The plant (shown in FIG. 1) for carrying out the process described above comprises successively:

a zone 1 for selective hydrogenation with simultaneous isomerisation of alpha olefins to internal olefins, said zone comprising at least one means 5 for introducing a cut to be converted, at least one means 12 for discharging an effluent and at least one means 6 for introducing hydrogen, said zone also comprising at least one catalyst bed which preferably comprises at least one metal selected from the group formed by nickel, palladium and platinum, deposited on a support;

an etherification and separation zone 2 comprising at least one means 12 for introducing effluent from zone 1 at least one means 7 for introducing an alcohol, at least one means 8 for discharging alcohol and/or an ether, and at least one means 13 for discharging an effluent which is practically free of alcohol and ether, the etherification zone containing at least one acid catalyst;

a zone 3 for separating oxygen-containing impurities, containing at least one capture mass for said compounds, and comprising at least one means 13 for introducing effluent from zone 2, and at least one means 14 for discharging the effluent produced;

a metathesis zone 4 containing at least one catalyst, preferably based on rhenium oxide deposited on a support, and comprising at least one means 14 for introducing an effluent from zone 3, at least one means 9 for introducing ethylene, at least one means 10 for discharging propylene and at least one means 11 for discharging by-products.

In the embodiment shown in FIG. 2, the plant of the invention comprises:

a zone 1 for selective hydrogenation with simultaneous isomerisation of alpha olefins to internal olefins, said zone comprising at least one means 5 for introducing a C₄ cut to be converted and at least one means 15' for introducing a mixture of isobutene and 1-butene, at least one means 12 for discharging an effluent and at least one means 6 for introducing hydrogen, said zone also comprising at least one catalyst bed which preferably comprises at least one metal selected from the group formed by nickel, palladium and platinum, deposited on a support;

an etherification and separation zone comprising at least one means 12 for introducing effluent from zone 1, at least one 7 for introducing an alcohol, at least one means 8 for discharging alcohol and/or an ether, and at least one means 13 for discharging an effluent which is practically free of alcohol and ether, the etherification zone containing at least one acid catalyst;

a zone 3 for separating oxygen-containing impurities, containing at least one capture mass for said compounds, and comprising at least one means 13 for introducing effluent from zone 2, and at least one means 14 for discharging the effluent produced;

a metathesis zone 4 containing at least one catalyst, preferably based on rhenium oxide deposited on a support, and comprising at least one means 14 for introducing effluent from zone 3, at least one means 9 for introducing ethylene, at least one means 10 for discharging propylene and at least one means 11 for discharging by-products;

a zone 1' for selective hydrogenation with simultaneous isomerisation of alpha olefins to internal olefins, said zone comprising at least one means 5' for introducing a C₅ cut to be converted, at least one means 12' for discharging an effluent and at least one means 6' for introducing hydrogen, said zone also comprising at least one catalyst bed which preferably comprises at least one metal selected from the group formed by nickel, palladium and platinum, deposited on a support;

an etherification and separation zone 2' comprising at least one means 12' for introducing effluent from zone 1', at least one means 7' for introducing an alcohol, at least one means 8' for discharging alcohol and/or an ether, and at least one means 13' for discharging an effluent which is practically free of alcohol and ether, the etherification zone containing at least one acid catalyst;

a zone 3' for separating oxygen-containing impurities, containing at least one capture mass for said compounds, and comprising at least one means 13' for introducing effluent from zone 2', and at least one means 14' for discharging the effluent produced;

a metathesis zone 4' containing at least one catalyst, preferably based on rhenium oxide deposited on a support, followed by a separation zone, and comprising at least one means 14' for introducing effluent from zone 3', at least one means 9' for introducing ethylene, at least one means 10' for discharging propylene, at least one means 15' for discharging a mixture of 1-butene and isobutene and at least one means 11' for discharging by-products.

The plant shown in FIG. 3 comprises zones 1, 2, 3, 4, 1' and 4' described above for FIG. 2, and does not contain zones 2' and 3'.

FIG. 4 shows the plant of FIGS. 2 and 3 but wherein metathesis zone 4 is provided with a means 14 for introducing effluent from zone 3 and a means 14' for introducing effluent from zone 3' (FIG. 2) or 12' for effluent from zone 1' (FIG. 3).

In a first embodiment, at least one etherification and separation zone comprises an etherification zone followed by at least one separation zone. Advantageously, the etherification zone contains an expanded catalyst bed.

In a preferred embodiment, at least one etherification and separation zone is a reactive distillation zone containing catalyst and in which the ether and alcohol are separated simultaneously with etherification.

Preferably, the metathesis zone is operated using a mobile catalyst bed.

In one particular embodiment, the C₄ and C₅ cuts originate from an upstream steam cracking zone, the means for introducing the cuts to be converted into zone 1 (1') being connected to said steam cracking zone, and the means for introducing ethylene into zone 4 (4') being connected to said steam cracking zone.

The following examples illustrate the invention without limiting its scope.

EXAMPLE 1

A C₄ cut leaving a steam cracker had the composition shown in Table 1 (stream 1). The following abbreviations were used in the Table: MTBE=methyltertiobutylether;

MAPD=methylacetylene+propadiene; BBV=1,2-butadiene+1-butyne+vinylacetylene; DME=dimethylether.

Firstly, the $C_4$ cut was hydroisomerised. It was continuously introduced at the mass flow rate shown in Table 1 and at a pressure of 2 MPa into a first reactor comprising a fixed bed of 2.6 T of a catalyst constituted by palladium on alumina which had been sulphurized. Hydrogen (mixed with methane) was also injected into the reactor as shown in Table 1 (stream 2). The temperature, which was 50° C. at the inlet, had risen to 95° C. at the outlet. The effluent was then treated in a finishing reactor charged with 2.5 T of the same catalyst and operating practically isothermally at 70° C. At the outlet (Table 1, stream 3), the cut was free of acetylenic compounds and the 1,3-butadiene had been transformed mainly into butenes, the majority of which were 2-butenes, since the 1-butene had been isomerised. The cut was then treated in a stabilizing column where the residual hydrogen and methane were separated. After this treatment, the cut had the composition of stream 4 (Table 1).

In the second step, the cut was etherified with methanol. It was mixed with methanol at the inlet to a group of two reactors disposed in series and charged with 25 m³ of a catalyst constituted by a cationic resin in its sulphonic acid form (Amberlyst 15 or equivalent). The mixture of the cut and methanol (Table 1, stream 5) was introduced into the bottom of the first reactor which operated as an expanded bed, with external recirculation through a heat exchanger at a pressure of 1.9 MPa. The temperature was 70° C. the effluent from the first step entered into the second reactor which operated as a fixed bed at 50° C. At the outlet, the crude etherification product (Table 1, stream 6) was distilled to separate the MTBE and the $C_4$ cut which was depleted in isobutene which contained a little methanol, and which was washed with water to extract the methanol which was recycled. The remaining $C_4$ cut had the composition shown in Table 1, stream 7.

This cut contained small amounts of oxygen-containing compounds which were captured by passage over a retaining bed constituted by 20 T of type 13X molecular sieve. Adsorption was carried out at a temperature of about 40° C. The composition of the effluent is shown in Table 1, stream 8.

In the final step, the residual cut, which contained mainly 2-butenes, was reacted with ethylene (overall composition: stream 9 in Table 1) over a metathesis catalyst constituted by rhenium oxide on gamma alumina (8% by weight of rhenium metal), prepared as described in U.S. Pat. No. 4,795,734. The $C_4$ cut was mixed at the inlet to the metathesis reactor with additional ethylene and with the ethylene and butene recycling streams. This reactor operated as a mobile bed as described in French patent FR-A-2 608 595, at a temperature of 35° C. and at a pressure of 3.5 MPa, and was coupled with a regenerator operating at 550° C. at atmospheric pressure. The catalyst was extracted at regular intervals from the bottom of the reactor and transferred to the regenerator from which it was returned to the top of the reactor, the transfers taking place via buffering traps. At the reactor outlet, unconverted ethylene was fractionated in a first distillation column and recycled. A second distillation column separated the propylene and a third column separated the unconverted $C_4$ hydrocarbons which were also recycled, along with small quantities of pentenes. The composition of the metathesis effluent is shown in Table 1, stream 10.

The overall balance of the transformation was determined as follows. For 100 parts by weight (pw) of C4 cut leaving the steam cracker, 1.6 pw of hydrogen, 14.9 pw of methanol and 27.1 pp of ethylene were consumed, and 40.9 pw of MTBE and 81.6 pw of propylene were produced. For the steam cracker from which the treated $C_4$ cut originates, this balance thus represents a small consumption of ethylene, and a large additional production of propylene, without having to modify the operating conditions of the cracker.

EXAMPLE 2

A $C_5$ cut at the outlet to a steam cracker had the composition shown in Table 2 (stream 1). The following abbreviations were used in the Table: TAME=methyl-tertioamylether; DME=dimethylether.

In the first hydrogenation and hydroisomerisation step 1, the $C_5$ cut was continuously introduced at the mass flow rate shown in Table 2 and at a pressure of 2 MPa into a first reactor comprising a fixed bed of 1.2 T of a catalyst constituted by palladium on alumina which had been sulphurized. Hydrogen (mixed with methane) was also injected into the reactor, as shown in Table 2 (stream 2). The temperature, which was 50° C. at the inlet, had risen to 85° C. at the outlet. The effluent was then treated in a finishing reactor charged with 1.1 T of the same catalyst and operating practically isothermally at 80° C. At the outlet (Table 2, stream 3), the cut was free of traces of acetylenic compounds and the $C_5$ diolefins had been hydrogenated to methyl-butenes and pentenes, the majority of which were 2-methyl-2-butene and 2-pentene due to the isomerisation which had occurred at the same time. The cut was then treated in a stabilizing column where the residual hydrogen and methane were separated. After this treatment, the cut had the composition of stream 4 (Table 2).

In the second step, the cut was etherified with methanol. It was mixed with methanol at the inlet to a group of two reactors disposed in series and charged with 15 m³ of a catalyst constituted by a cationic resin in its sulphonic acid form (Amberlyst 15 or equivalent). The mixture of the cut and methanol (Table 2, stream 5) was introduced into the bottom of the first reactor which operated as an expanded bed, with external recirculation through a heat exchanger at a pressure of 1 MPa. The temperature was 70° C. The effluent from the first step entered into the second reactor which operated as a fixed bed at 50° C. At the outlet, the crude etherification product (Table 2, stream 6) was distilled to separate the TAME and the $C_5$ cut which was depleted in methyl-butenes which still contained a little methanol. The remaining $C_5$ cut had the composition shown in Table 2, stream 7.

This cut contained small amounts of oxygen-containing compounds which were captured by passage over a retaining bed constituted by 10 T of type 13X molecular sieve. Adsorption was carried out at a temperature of about 40° C. The composition of the effluent is shown in Table 2, stream 8.

In the final step, the residual cut was reacted with ethylene (overall composition: stream 9 in Table 2) over a metathesis catalyst constituted by rhenium oxide on gamma alumina (8% by weight of rhenium metal), prepared as described in U.S. Pat. No. 4,795,734 The metathesis reactor operated as a mobile bed as described in French patent FR-A-2 608 595, at a temperature of 35° C. and at a pressure of 3.5 MPa, and was coupled with a regenerator operating at 550° C. at atmospheric pressure. The catalyst was extracted at regular intervals from the bottom of the reactor and transferred to the regenerator from which it was returned to the top of the reactor, the transfers taking place via buffering traps. At the reactor outlet, unconverted ethylene was fractionated in a first distillation column and recycled. A second distillation column separated the propylene and a third column separated the isobutene and 1-butene overhead and the heavier olefins at the bottom. The composition of the metathesis effluent is shown in Table 2, stream 10.

The overall balance of the transformation was determined as follows. For 100 parts by weight (pw) of $C_5$ cut leaving the steam cracker, 1 pw of hydrogen, 7.9 pw of methanol and 8.5 pw of ethylene were consumed, and 25 pw of TAME, 8.3 pw of propylene, 4.4 pw of isobutene and 6.7 pw of 1-butene were produced.

EXAMPLE 3

This Example describes the use of both a $C_4$ and a $C_5$ steam cracking cut to produce MTBE and propylene.

The same $C_5$ cut from the steam cracker as that described in Example 2 was used here to maximise the quantity of isobutene formed after metathesis, by omitting the etherification step and thus the oxygen-containing compound separation step. Thus it successively underwent the steps of hydroisomerisation, then a metathesis step in the presence of ethylene, under the same conditions and using the same catalysts as those described in Example 2.

The balance of this operation is shown in Table 3. The stream of isobutene and 1-butene obtained after fractionation of the crude effluent from the metathesis step was then mixed with the $C_4$ cut used in Example 1. The mixture then underwent the same succession of steps under the same conditions as those described in Example 1. The balance for this operation is shown in Table 4.

The overall balance of the transformation was determined as follows. For 69 parts by weight (pw) of $C_4$ cut and 31 parts by weight (pw) of $C_5$ cut leaving the steam cracker, 1.5 pw of hydrogen, 12.4 pw of methanol and 23.8 pw of ethylene were consumed, and 34.2 pw of MTBE and 64.4 pw of propylene were produced.

TABLE 1

| (kg/h) | 1 Feed $C_4$ | 2 Feed hydro-isomerisation | 3 Outlet hydro-isomerisation | 4 $C_4$ Outlet stabilisation | 5 Inlet MTBE | 6 Outlet MTBE | 7 $C_4$ inlet oxygen-containing separation | 8 $C_4$ outlet oxygen-containing separation | 9 Inlet metathesis | 10 Outlet metathesis |
|---|---|---|---|---|---|---|---|---|---|---|
| (C3 + C3=) | 10 | 10 | 45 | 28 | 28 | 28 | | | | |
| MAPD | 31 | 31 | | | | | | | | |
| Iso + n-butane | 991 | 991 | 1434 | 1404 | 1404 | 1404 | 1404 | 1404 | 1404 | 1404 |
| Isobutene | 5741 | 5741 | 5741 | 5533 | 5533 | 165 | 165 | 165 | 165 | 165 |
| 1-butene | 3407 | 3407 | 1003 | 729 | 729 | 729 | 729 | 729 | 729 | 445 |
| 2-butenes | 2250 | 2250 | 12733 | 12630 | 12630 | 12630 | 12630 | 12630 | 12630 | 1270 |
| 1,3-butadiene | 8095 | 8095 | | | | | | | | |
| BBV | 104 | 104 | | | | | | | | |
| Hydrogen | | 343 | 16 | | | | | | | |
| Methane | | 909 | 909 | | | | | | | |
| Methanol | | | | | 3070 | 0.7 | 0.7 | | | |
| MTBE | | | | | | 8433 | 0.4 | | | |
| DME | | | | | | 4 | 4 | | | |
| Ethylene | | | | | | | | | 5594 | 56 |
| Propylene | | | | | | | | | | 16827 |
| Pentenes | | | | | | | | | | 355 |
| Total | 20629 | 21881 | 21881 | 20324 | 23394 | 23394 | 14933 | 14928 | 20522 | 20522 |

TABLE 2

| (kg/h) | 1 Feed $C_5$ | 2 Feed hydro-isomerisation | 3 Outlet hydro-isomerisation | 4 $C_5$ outlet stabilisation | 5 Inlet TAME | 6 Outlet TAME | 7 $C_5$ inlet oxygen-containing separation | 8 $C_5$ outlet oxygen-containing separation | 9 Inlet metathesis | 10 Outlet metathesis |
|---|---|---|---|---|---|---|---|---|---|---|
| C4 | 91 | 91 | 91 | 91 | 91 | 91 | | | | |
| C5 dienes | 2723 | 2723 | | | | | | | | |
| Iso + n-pentane | 4538 | 4538 | 4729 | 4729 | 4729 | 4729 | 4729 | 4729 | 4729 | 4729 |
| 3-methyl-1-butene | 61 | 61 | 34 | 34 | 34 | 34 | 34 | 34 | 34 | 34 |
| 2-methyl-1-butene | 294 | 294 | 156 | 156 | 156 | 47 | 47 | 47 | 47 | 47 |
| 2-methyl-2-butene | 734 | 734 | 2070 | 2070 | 2070 | 622 | 622 | 622 | 622 | 124 |
| 1-pentene | 248 | 248 | 119 | 119 | 119 | 119 | 119 | 119 | 119 | 119 |

TABLE 2-continued

| (kg/h) | 1 Feed $C_5$ | 2 Feed hydro-isomerisation | 3 Outlet hydro-isomerisation | 4 $C_5$ outlet stabilisation | 5 Inlet TAME | 6 Outlet TAME | 7 $C_5$ inlet oxygen-containing separation | 8 $C_5$ outlet oxygen-containing separation | 9 Inlet metathesis | 10 Outlet metathesis |
|---|---|---|---|---|---|---|---|---|---|---|
| 2-pentene | 252 | 252 | 1174 | 1174 | 1174 | 1174 | 1174 | 1174 | 1174 | 411 |
| Other $C_5$ olefins | 136 | 136 | 788 | 788 | 788 | 788 | 788 | 788 | 788 | 158 |
| Hydrogen |  | 88 | 4 |  |  |  |  |  |  |  |
| Methane |  | 177 | 177 |  |  |  |  |  |  |  |
| Methanol |  |  |  |  | 715 | 1 | 1 |  |  |  |
| TAME |  |  |  |  |  | 2269 | 0.5 |  |  |  |
| DME |  |  |  |  |  | 2 | 2 |  |  |  |
| Ethylene |  |  |  |  |  |  |  |  | 771 | 8 |
| Propylene |  |  |  |  |  |  |  |  |  | 757 |
| Isobutene |  |  |  |  |  |  |  |  |  | 359 |
| 1-butene |  |  |  |  |  |  |  |  |  | 610 |
| Heavy > $C_5$ |  |  |  |  |  |  |  |  |  | 928 |
| Total | 9077 | 9342 | 9342 | 9161 | 9876 | 9876 | 7517 | 7513 | 8284 | 8284 |

TABLE 3

| (kg/h) | 1 Feed $C_5$ | 2 Feed hydroisomerisation | 3 Outlet hydroisomerisation | 4 $C_5$ Outlet stabilisation | 5 Inlet metathesis | 6 Outlet metathesis |
|---|---|---|---|---|---|---|
| $C_4$ | p11 91 | 91 | 91 | 91 |  |  |
| $C_5$ dienes | 2723 | 2723 |  |  |  |  |
| Iso + n-pentane | 4538 | 4538 | 4729 | 4729 | 4729 | 4729 |
| 3-methyl-1-butene | 61 | 61 | 34 | 34 | 34 | 34 |
| 2-methyl-1-butene | 294 | 294 | 156 | 156 | 156 | 156 |
| 2-methyl-2-butene | 734 | 734 | 2070 | 2070 | 2070 | 414 |
| 1-pentene | 248 | 248 | 119 | 119 | 119 | 119 |
| 2-pentene | 252 | 252 | 1174 | 1174 | 1174 | 411 |
| Other $C_5$ olefins | 136 | 136 | 788 | 788 | 788 | 158 |
| Hydrogen |  | 88 | 4 |  |  |  |
| Methane |  | 177 | 177 |  |  |  |
| Ethylene |  |  |  |  | 1238 | 12 |
| Propylene |  |  |  |  |  | 1451 |
| Isobutene |  |  |  |  |  | 1193 |
| 1-butene |  |  |  |  |  | 610 |
| Heavy > $C_5$ |  |  |  |  |  | 1021 |
| Total | 9077 | 9342 | 9342 | 9161 | 10308 | 10308 |

TABLE 4

| (kg/h) | 1 Feed $C_4$ | 2 $C_4$ from metathesis of $C_5$ | 3 Feed hydro-isomerisation | 4 Outlet hydro-isomerisation | 5 Inlet MTBE | 6 Outlet MTBE | 7 $C_4$ inlet oxygen-containing separation | 8 $C_4$ outlet oxygen-containing separation | 9 Inlet metathesis | 10 Outlet metathesis |
|---|---|---|---|---|---|---|---|---|---|---|
| (C3 + C3=) | 10 |  | 10 | 45 | 28 | 28 |  |  |  |  |
| MAPD | 31 |  | 31 |  |  |  |  |  |  |  |
| Iso + n-butane | 991 |  | 991 | 1434 | 1434 | 1434 | 1434 | 1434 | 1434 | 1434 |

TABLE 4-continued

| (kg/h) | 1 Feed C$_4$ | 2 C$_4$ from metathesis of C$_5$ | 3 Feed hydro-isomerisation | 4 Outlet hydro-isomerisation | 5 Inlet MTBE | 6 Outlet MTBE | 7 C$_4$ inlet oxygen-containing separation | 8 C$_4$ outlet oxygen-containing separation | 9 Inlet metathesis | 10 Outlet metathesis |
|---|---|---|---|---|---|---|---|---|---|---|
| Isobutene | 5741 | 1193 | 6934 | 6934 | 6934 | 198 | 198 | 198 | 198 | 198 |
| 1-butene | 3407 | 610 | 4017 | 1047 | 1047 | 1047 | 1047 | 1047 | 1047 | 639 |
| 2-butenes | 2250 | | 2250 | 13310 | 13310 | 13310 | 13310 | 13310 | 13310 | 1308 |
| 1,3-butadiene | 8095 | | 8095 | | | | | | | |
| BBV | 104 | | 104 | | | | | | | |
| Hydrogen | | | 350 | 12 | | | | | | |
| Methane | | | 909 | 909 | | | | | | |
| Methanol | | | | | 3854 | 1 | 1 | | | |
| MTBE | | | | | | 10585 | 1 | | | |
| DME | | | | | | 4 | 4 | | | |
| Ethylene | | | | | | | | | 5840 | 58 |
| Propylene | | | | | | | | | | 17682 |
| Pentenes | | | | | | | | | | 510 |
| Total | 20629 | 1803 | 23691 | 23691 | 26607 | 26607 | 15995 | 15989 | 21829 | 21829 |

What is claimed is:

1. A plant for converting an olefinic cut, selected from the group consisting of a C$_4$ cut and a C$_5$ cut, to an ether and to propylene, comprising successively:

1) a first selective hydrogenation zone for selective hydrogenation of acetylene and diolefinic impurities with simultaneous isomerisation of alpha olefins, said first selective hydrogenation zone comprising at least one means for introducing a cut to be converted, at least one means for discharging an effluent and at least one means for introducing hydrogen, said first selective hydrogenation zone also comprising at least one catalyst bed for said selective hydrogenation and isomerization;

2) at least one etherification and ether separation zone comprising at least one means for introducing effluent from the first selective hydrogenation zone, at least one means for introducing an alcohol, at least one means for discharging alcohol and/or an ether, and at least one means for discharging an effluent depleted in alcohol and ether, the etherification zone containing at least one acid etherification catalyst; said ether separation zone following said etherification zone comprising a distillation section for separating the resultant ether from a distillate of residual olefins, excess alcohol and volatile oxygen-containing compounds;

3) a first oxygen-containing impurity separation zone containing at least one mass for capturing said further oxygen-containing impurities, and comprising at least one means for introducing effluent from etherification and ether separation zone, and at least one means for discharging the effluent produced;

4) a first metathesis zone containing at least one catalyst, followed by a propylene separation zone, and comprising at least one means for introducing said effluent from the first oxygen-containing impurity separation zone, at least one means for introducing ethylene, at least one means, for discharging propylene and at least one means for discharging by-products, said propylene separation-zone comprising a distillation section for separating the propylene from unconverted hydrocarbons, said plant further successively comprising a second selective hydrogenation zone, a second etherification and ether separation zone, a second oxygen-containing impurities separation zone and a second metathesis zone to treat a C$_5$ cut introduced into the second selective hydrogenation zone via a line, a second metathesis zone being provided with a line for discharging a mixture of 1-butene and isobutene which is connected to the first selective hydrogenation zone to introduce said mixture into the first selective hydrogenation zone.

2. A plant according to claim 1, said first metathesis zone being provided with means for introducing effluent from the first oxygen-containing impurities separation zone and means for introducing effluent from the second oxygen-containing impurities separation zone.

3. A plant according to claim 1, wherein at least one etherification and ether separation zone comprises an etherification zone followed by at least one separation zone.

4. A plant according to claim 1, wherein the etherification catalyst is in the form of an expanded catalyst bed.

5. A plant according to claim 1, wherein at least one etherification and separation zone is a reactive distillation zone containing the catalyst and in which separation of the ether and the alcohol takes place simultaneously with etherification.

6. A plant according to claim 1, characterized in that the metathesis zone contains a mobile catalyst bed.

7. A plant according to claim 1, said first oxygen-containing impurity separation zone (3) further comprising means for regenerating said at least one mass after said mass is saturated with oxygen-containing and/or sulfur-containing impurities.

8. A plant according to claim 1, wherein said propylene distillation section comprises a first distillation column for separating ethylene and means for recycling said ethylene to the metathesis zone, a second distillation column for separating the propylene, and a third distillation column for separating unconverted $C_4$ hydrocarbon and further recycle means for recycling said unconverted $C_4$ hydrocarbons to said metathesis zone.

9. A plant according to claim 1, further comprising means for washing said distillate from the first etherification and ether separation zone to recover a mixture of water and alcohol, and means for distilling said mixture to recover said alcohol, and means for recycling said alcohol to the etherification zone.

10. A plant according to claim 8, further comprising means for washing said distillate from the first etherification and ether separation zone to recover a mixture of water and alcohol, and means for distilling said mixture to recover said alcohol, and means for recycling said alcohol to the etherification zone.

11. A plant according to claim 1, wherein said means for introducing effluent from the first etherification and ether separation zone into the first oxygen-containing impurities separation zone comprises means for introducing bottom effluent from a distillation column.

12. A plant according to claim 1, wherein said means for introducing effluent from the first etherification and ether separation zone into the first oxygen-containing impurities separation zone comprises means for introducing top effluent from a distillation column.

13. A plant for converting an olefinic cut, selected from the group consisting of a $C_4$ cut and a $C_5$ cut, to an ether and to propylene, comprising successively:

1) a first selective hydrogenation zone for selective hydrogenation of acetylene and diolefinic impurities with simultaneous isomerisation of alpha olefins, said first selective hydrogenation zone comprising at least one means for introducing a cut to be converted, at least one means for discharging an effluent and at least one means for introducing hydrogen, said first selective hydrogenation zone also comprising at least one catalyst bed for said selective hydrogenation and isomerization;

2) at least one etherification and ether separation zone comprising at least one means for introducing effluent from the first selective hydrogenation zone, at least one means for introducing an alcohol, at least one means for discharging alcohol and/or an ether, and at least one means for discharging an effluent depleted in alcohol and ether, the etherification zone containing at least one acid etherification catalyst; said ether separation zone following said etherification zone comprising a distillation section for separating the resultant ether from a distillate of residual olefins, excess alcohol and volatile oxygen-containing compounds;

3) a first oxygen-containing impurity separation zone containing at least one mass for capturing said further oxygen-containing impurities, and comprising at least one means for introducing effluent from one etherification and ether separation zone, and at least one means for discharging the effluent produced;

4) a first metathesis zone containing at least one catalyst, followed by a propylene separation zone, and comprising at least one means for introducing said effluent from the first oxygen-containing impurity separation zone, at least one means for introducing ethylene, at least one means, for discharging propylene and at least one means for discharging by-products, said propylene separation-zone comprising a distillation section for separating the propylene from unconverted hydrocarbons, said plant further successively comprising a second selective hydrogenation zone and a second metathesis zone to treat a $C_5$ cut introduced via a line for discharging a mixture of 1-butene and isobutene which is connected to the first selective hydrogenation zone, to introduce said mixture into the first selective hydrogenation zone.

14. A plant according to claim 13, said first metathesis zone being provided with means for introducing effluent from the first oxygen-containing impurities separation zone, and means for introducing effluent from the first hydrogenation zone.

* * * * *